United States Patent
Grantz et al.

[11] Patent Number: 5,980,485
[45] Date of Patent: Nov. 9, 1999

[54] PRESSURE-SENSITIVE BALLOON CATHETER

[75] Inventors: Stephen M. Grantz, Pelham, N.H.; John Hudson, Wells, Me.

[73] Assignee: Medtronics AVE, Inc., Santa Rosa, Calif.

[21] Appl. No.: 09/042,232

[22] Filed: Mar. 13, 1998

[51] Int. Cl.$^6$ .................................................. A61M 29/00
[52] U.S. Cl. ............................................. 604/96; 606/194
[58] Field of Search .................................. 604/96, 97, 99, 604/100; 606/191, 192, 194

[56] References Cited

U.S. PATENT DOCUMENTS

| | | |
|---|---|---|
| 3,662,592 | 5/1972 | Geisler . |
| 3,800,598 | 4/1974 | Michel . |
| 5,102,402 | 4/1992 | Dror et al. . |
| 5,458,571 | 10/1995 | Lampropoulos et al. . |
| 5,624,450 | 4/1997 | Glastra . |
| 5,674,242 | 10/1997 | Phan et al. . |
| 5,720,762 | 2/1998 | Bass . |
| 5,766,151 | 6/1998 | Valley et al. . |

*Primary Examiner*—Corrine McDermott
*Attorney, Agent, or Firm*—Sterne, Kessler, Goldstein & Fox P.L.L.C.

[57] ABSTRACT

A pressure-sensitive balloon catheter includes a material that undergoes a visible color change when exposed to the pressures experienced in an angioplasty or a stent placement procedure. By removing the balloon catheter and verifying the color change and the patterns of colors on the balloon, a physician can verify that proper amounts of pressure were applied to all portions of a patient's artery or a stent within a patient's artery.

31 Claims, 2 Drawing Sheets

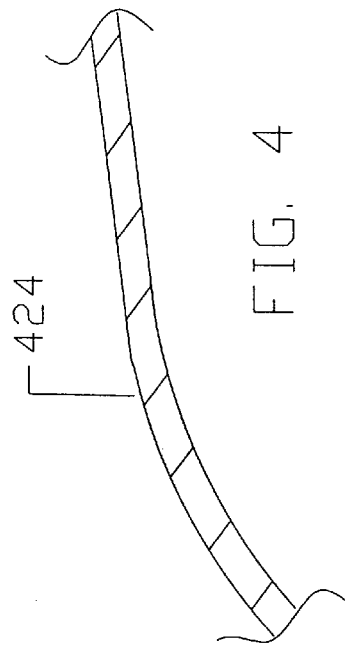
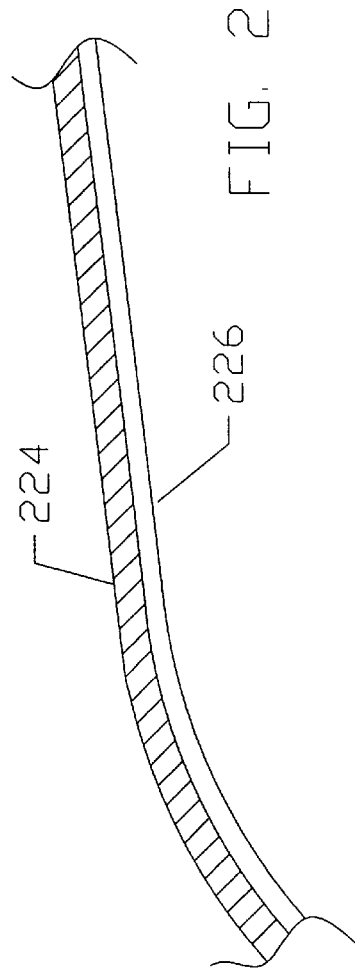
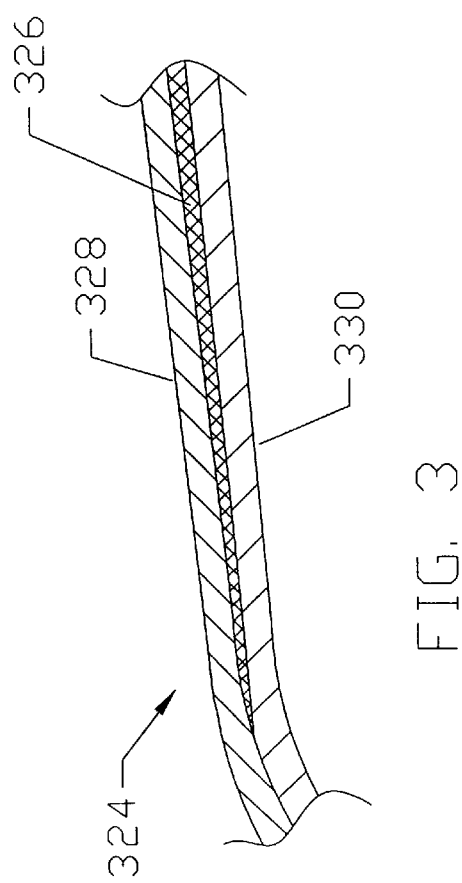

PRESSURE-SENSITIVE BALLOON CATHETER

FIELD OF THE INVENTION

The invention relates to a pressure-sensitive balloon catheter for use in angioplasty, stent placement, and related procedures, and more particularly to a balloon catheter that permits a reliable visual determination of the pressure exerted against an anatomical feature or other device during a medical procedure.

BACKGROUND OF THE INVENTION

Heart disease currently is a leading cause of death and disability among adults. One type of heart disease, atherosclerosis, is particularly common. Atherosclerosis, a disease of the coronary arteries, is characterized by a thickening of the lining of the coronary arteries, from the deposit of fatty substances such as cholesterol. When this occurs, the inner diameter of the coronary arteries is reduced, and so is the blood flow to the heart. This can cause an insufficient amount of oxygen to reach the heart, particularly during periods of exercise or other exertion. Atherosclerosis can reach a relatively advanced stage before its presence is indicated by symptoms in the patient. However, when symptoms occur, they can be extremely serious. Atherosclerosis can result in angina, or heart pain, or in the most severe circumstances, a heart attack.

There are several widely-accepted treatments for atherosclerosis. One treatment, which is rather invasive, is a coronary bypass. In this procedure, a less-damaged portion of artery, or a segment of synthetic material, is inserted into the patient's coronary artery system to bypass the clogged portion. This typically involves open-heart surgery, which can be extremely traumatic to the patient. Moreover, this type of surgery has a number of serious risks. Finally, such an operation typically requires an extended recovery period.

Another treatment for atherosclerosis is angioplasty, which has been practiced for the last approximately thirty years. Formally known as "percutaneous transluminal coronary angioplasty," or "PTCA," angioplasty involves the insertion of a catheter through an incision in the patient's skin, and advancement of the catheter into the vascular system and toward a blocked coronary artery. When the target is reached, a balloon structure at the distal end of the catheter is inflated and deflated, once or several times, to compress the plaque on the artery wall and stretch the blood vessel, thereby enlarging the diameter of the artery. The enlargement is usually maintained after completion of the procedure by a regulated amount of damage having been done to the elastin and collagen in the vessel.

Angioplasty has some notable disadvantages, however. In many cases, the patient's artery will eventually narrow again. This occurrence is known as restenosis. And in a relatively small percentage of patients, the opened artery will reclose almost immediately after the angioplasty is performed. In such cases, further procedures must be undertaken to reopen the patient's artery; these procedures might include further angioplasty, but when angioplasty has proven to be unsuccessful, open-heart surgery (such as a coronary bypass operation) may become necessary.

It has been found, however, that using an optimum amount of pressure against the artery during the angioplasty procedure will result in the smallest incidence of complications. However, although it may be possible to determine the total amount of pressure being applied to the entire artery wall (for example, by examining the fluid pressure required to inflate the balloon), it is difficult to determine how much pressure has been applied to any particular portion of the blockage.

A treatment related to angioplasty that has become popular within the last three years involves the placement of a reinforcing member known as a "stent" into the damaged coronary artery. A stent is usually a metallic tube-shaped structure that serves as scaffolding, preventing the artery from closing down to its previous size after the procedure is performed. After the procedure is complete, the stent is left in place.

Typically, in a stent implantation operation, a PTCA procedure is performed first, to enlarge the diameter of a clogged portion of a coronary artery. Then, a stent is inserted over a balloon catheter, maneuvered into place, and the balloon is inflated to expand the stent and anchor it into place.

Although many different stent types and configurations are available, a typical stent known as a "Palmaz" stent is formed from a metallic mesh that is deformable to expand and maintain a desired diameter.

Although the placement of a stent may, in many cases, reduce the incidence of acute artery reclosing, and may also reduce the difficulties of restenosis, there are other difficulties and side-effects that can occur when a stent is implanted. First, the stent may perforate the blood vessel if an improper or inconsistent amount of force is applied to inflate the balloon catheter and expand the stent. Second, the position of a stent is difficult to adjust after placement, and it may migrate somewhat in the time shortly after its placement (but typically not later, as the lining of the artery tends to grow over the stent within a period of weeks). Thus, it is particularly important to properly locate and expand the stent when it is first implanted. Third, the existence of a stent in a patient's coronary arteries may result in thrombosis, or the creation of undesired blood clots.

However, it has been found that the accurate placement and deployment of a stent will reduce the incidence of many complications. For example, the inadequate expansion of a stent may cause turbulent blood flow around the stent, resulting in thrombosis. Moreover, in such a case, there would also be additional exposure of the stent material to the blood stream, and any inherent thrombogenicity, or tendency to cause blood clots, of the stent material might be enhanced. Finally, ensuring that the proper amount of pressure is applied to expand the stent will reduce the incidence of perforation. Unfortunately, it is difficult to tell via angiographic fluoroscopy (i.e., X-rays), whether a stent is accurately located and sufficiently expanded with respect to a particular identified blockage.

Consequently, there is a need for a balloon catheter system that permits the accurate determination of whether a sufficient amount of pressure has been applied to adequately expand all parts of the treated coronary artery, or to properly locate and expand a coronary stent. Such a system would reduce the "guesswork" that otherwise is necessary in angioplasty and stent-placement procedures.

SUMMARY OF THE INVENTION

The balloon catheter described herein is pressure-sensitive, and reacts by changing color when a threshold level of pressure is applied. It is thus capable of being "read" before an angioplasty or stent-placement procedure is completed. A traditionally configured balloon catheter according to the invention has a pressure-sensitive balloon. When pressure is applied to the balloon, a pattern of color change proportional to the amount of pressure applied to any portion of the balloon becomes visible.

Accordingly, when a balloon catheter embodying the invention is used and removed from a patient, a pattern of coloration on the pressure-sensitive balloon shows the contact between the balloon and the patient's artery (or a stent), including an indication of the continuous pressure applied across the entire surface of the balloon.

While it is known in the art to measure the pressure utilized in inflating a balloon in a dilatation operation in order to estimate the pressure that is being applied to a patient's anatomical features, this information has been imprecise, and has been limited to a "global" reading of average pressure. With a pressure-sensitive balloon made according to the invention, individual areas of high and low pressure can be identified by observing colored patterns, or patches, on the balloon. This information can be used to determine whether insufficient pressure, excessive pressure, or inconsistent pressure was applied during an angioplasty procedure or when deploying a stent; corrective measures can then be taken as necessary.

BRIEF DESCRIPTION OF THE DRAWINGS

FIG. 2 is a sectional view of the catheter of FIG. 1, in which the pressure-sensitive film is applied to an internal surface of the balloon;

FIG. 3 is a sectional view of the catheter of FIG. 1, in which the pressure-sensitive film is placed between two layers of the balloon; and FIG. 4 is a sectional view of the catheter of FIG. 1, in which the balloon is fabricated from pressure-sensitive material.

DETAILED DESCRIPTION OF THE INVENTION

Figure 1:
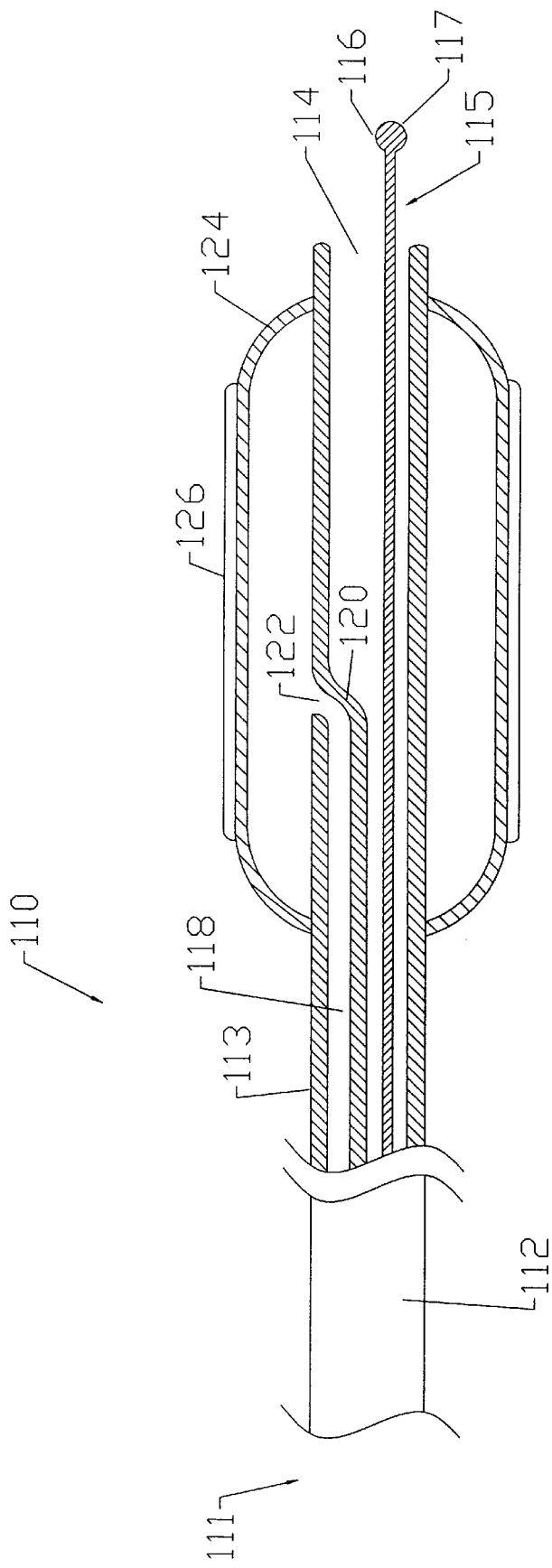
FIG. 1 is a partial longitudinal sectional view of a pressure-sensitive balloon catheter according to the invention, in which a balloon has an externally-applied pressure-sensitive film.

The invention is described below, with reference to detailed illustrative embodiments. It will be apparent that the invention can be embodied in a wide variety of forms, some of which may be quite different from those of the disclosed embodiments. Consequently, the specific structural and functional details disclosed herein are merely representative and do not limit the scope of the invention.

Referring initially to FIG. 1, a portion of a balloon catheter 110 bearing a pressure-sensitive covering is shown. In most ways, the balloon catheter of FIG. 1 is similar to traditional balloon catheters. For example, the catheter 110 has a shaft that is covered by a jacket 112. Under the jacket 112 is a primary wall 113, approximately tubular in configuration, that defines a longitudinal primary lumen 114 from a proximal end of the catheter 111 to a distal end 115. The primary lumen 114 accommodates a guidewire 116, which extends from the proximal end 111 of the catheter 110, through the primary lumen 114, and out the distal end 115.

The guidewire 116 is used to position the catheter 110 within the patient's vascular system. Once the guidewire has been maneuvered into the proper position, so that its distal end 117 is located at or beyond a target site in the patient's coronary arteries (or elsewhere), various other medical devices such as the balloon catheter 110 can be advanced and retracted over the guidewire.

The balloon catheter 110 also contains an inflation lumen 118, which is defined by the primary wall 113 and a secondary wall 120. The inflation lumen 118 is in fluid communication with the proximal end 111 of the catheter 110 and an expandable balloon 124 at the distal end 115 of the catheter 110 via an opening 122 defined between the primary wall 113 and the secondary wall 120. Fluid is advanced through the inflation lumen 118 to inflate the balloon 124, and removed to deflate the balloon 124. In a preferred embodiment of the invention, the balloon is made from a polymeric material that is able to withstand repeated inflation and deflation. Typical polymeric materials include polyethylene terephthalate (PET), nylons, polyurethanes, and mixtures and copolymers of these classes typical of balloon materials.

In a pressure-sensitive balloon catheter according to the invention, the balloon 124 bears a pressure-sensitive coating 126. The coating may be in the form of a pressure-sensitive adhesive film, or alternatively may be a coating deposited on the balloon. This coating has the characteristic that it changes in color, or other measurable physical characteristic, when it is exposed to a threshold level of pressure.

In one embodiment of the invention, a quantity of PRESSUREX film from Sensor Products, Inc. is placed on the outer surface of the balloon. This pressure-sensitive film comprises a multiple-layer structure. Between two layers of mylar substrate, a large number of microscopic "microcapsules" contain a colorless reactive agent. These microcapsules are positioned adjacent to a colorless developing layer, also between the substrate layers. When a threshold level of pressure is applied to the film, the microcapsules are caused to rupture. The material contained in the microcapsules mixes with the material of the developing layer, and a color change occurs. This color change can then be viewed and compared to a color chart to determine the pressure that was exerted against the film.

PRESSUREX film is available in a number of pressure ranges. However, it has been found the "ULTRA LOW" (28–85 psi) and "SUPER LOW" (70–350 psi) pressure ranges are particularly useful in balloon catheter applications. Furthermore, other brands and types of pressure-sensitive films and coatings would also be useful and applicable to the invention, provided that the available pressure ranges sufficiently match the ranges that are typically encountered in medical procedures using the balloon device. Moreover, whatever film or coating is used should be sufficiently flexible to accommodate the inflation and deflation of the balloon 124; alternatively, the film or coating can be cut or applied in small regions, allowing the balloon 124 to stretch and expand between those regions. And when applied to an external surface of a balloon 124, as in FIG. 1, the pressure-sensitive material should be substantially biocompatible to avoid any significant adverse effects arising from tissue or blood contact.

An alternate embodiment of the balloon catheter 110 is shown, in operative part, in FIG. 2. In this embodiment, the pressure-sensitive coating or film 226 is deposited on or adhered to an internal surface of the balloon 224. In this case, the pressure-sensitive material need not be biocompatible, as it is isolated from direct contact with the patient via the balloon 224. However, the material from which the balloon is made should be sufficiently transparent or translucent that any color change occurring in the coating or film 226 is visible outside the balloon 224. A further alternative embodiment is shown in FIG. 3. In this case, the pressure-sensitive material 326 is placed between two layers 328 and 330 of the balloon 324.

Finally, FIG. 4 shows an embodiment of the invention that does not employ any separate coating or film (such as the coating or film 126 in FIG. 1). Rather, the balloon 424 is fabricated from a material that incorporates the requisite pressure-sensing materials. For example, the balloon 424 could be impregnated with microcapsules, and the elastomeric material from which the balloon is formed can further contain the color developing material (provided both the developing material and the microcapsules are sufficiently biocompatible).

The pressure-sensitive balloon catheter 110 can be used in a variety of applications. For example, in an angioplasty procedure, the guidewire 116 (FIG. 1) is first advanced into location. The balloon catheter 110 is advanced over the guidewire 116 until the balloon 124 is located at the site of the coronary artery that is to be treated. The balloon 124 is then inflated to a pre-calculated pressure to expand the artery. The balloon 124 is then deflated, and the catheter 110 is removed from the patient while retaining the guidewire 116 in place. The balloon 124 is then cleaned and viewed to determine whether an appropriate pressure level was exerted within the artery.

If insufficient pressure was exerted, then the coating or film 126 will exhibit a lack of coloration; another catheter can then be inserted along the guidewire 116 to repeat the procedure, but with additional pressure or at a different location. If too much pressure was exerted, the film or coating 126 will exhibit dark coloration; steps can then be taken to ensure that the patient will not experience complications resulting from the excessive pressure. In certain circumstances, it may be necessary to immediately proceed with open-heart surgery. If the correct amount of pressure was exerted, then the film or coating 126 will exhibit a desired amount of coloration (which can be visually ascertained or compared to a color chart) in locations corresponding to the treated blockage.

In a stent-placement procedure, an angioplasty procedure typically is performed first; a pressure-sensitive balloon catheter can be used for this phase of the procedure as described above. After the target artery has been dilated (and the pressure employed in doing so optionally verified, as above, by checking the pressure-sensitive coating or film 126), the catheter 110 is removed from the guidewire 116, which is still in place, and replaced with a second catheter 110 which bears an unexpanded stent around the balloon 124. The second catheter is positioned, and the balloon is inflated, causing the stent to expand and anchor itself to the artery wall. Again, the second catheter is removed (while the stent remains in place), cleaned, and viewed to determine whether an appropriate pressure level was exerted to expand the stent.

The coating or film 126 will exhibit a pattern and level of coloration representative of the pressure exerted by the balloon 124 against the stent. If the pressure was too low, too high, or inconsistently applied (e.g., when the stent is improperly placed), then the coloration of the coating or film 126 will show it, and corrective measures can immediately be taken.

A specific embodiment of the invention has been described as used primarily in the context of coronary angioplasty. However, it should be recognized that the invention as claimed would be operative in any context in which a balloon device is used to dilate an anatomical feature or medical device, such as in urological applications, and should not strictly be limited to angioplasty.

What is claimed is:

1. A pressure-sensitive balloon catheter, comprising:

a catheter having a distal end;

a balloon mounted to the distal end of the catheter;

means for inflating the balloon; and a pressure-sensitive material fixedly associated with the balloon, wherein the pressure-sensitive material undergoes a change in a physical characteristic when exposed to pressure to indicate the amount of pressure applied to the balloon.

2. The pressure-sensitive balloon catheter of claim 1, wherein the pressure-sensitive material comprises a pressure-sensitive film.

3. The pressure-sensitive balloon catheter of claim 2, wherein the pressure-sensitive film is mounted on an outer surface of the balloon.

4. The pressure-sensitive balloon catheter of claim 2, wherein the pressure-sensitive film is mounted on an inner surface of the balloon.

5. The pressure-sensitive balloon catheter of claim 2, wherein:

the balloon comprises a first layer and a second layer; and the pressure-sensitive film is disposed between the first layer of the balloon and the second layer of the balloon.

6. The pressure-sensitive balloon catheter of claim 1, wherein the pressure-sensitive material comprises a pressure-sensitive coating.

7. The pressure-sensitive balloon catheter of claim 6, wherein the pressure-sensitive coating is disposed on an outer surface of the balloon.

8. The pressure-sensitive balloon catheter of claim 6, wherein the pressure-sensitive coating is disposed on an inner surface of the balloon.

9. The pressure-sensitive balloon catheter of claim 1, wherein the change in a physical characteristic is a change in color.

10. The pressure-sensitive balloon catheter of claim 9, wherein the change in color is visually perceptible.

11. The pressure-sensitive balloon catheter of claim 1, wherein the means for inflating comprises an inflation lumen in fluid communication with the balloon.

12. A pressure-sensitive balloon catheter, comprising:

a catheter having a distal end;

a pressure-sensitive balloon mounted to the distal end of the catheter, the balloon comprising dynamic, pressure-measuring indicia responsive to being subjected to a pressure above a predetermined threshold level to change a physical characteristic and thereby visually indicate the amount of pressure applied to the balloon; and means for inflating the balloon.

13. The pressure-sensitive balloon catheter of claim 12, wherein the pressure-measuring indicia comprises:

a translucent polymeric material:

a plurality of microcapsules disposed within the polymeric material, wherein said microcapsules are adapted to rupture upon the application of pressure; and a color developing material within the polymeric material.

14. A pressure-sensitive balloon catheter, comprising:

a catheter comprising an inflation lumen;

a balloon mounted to the catheter and in fluid communication with the inflation lumen; and wherein the balloon comprises a pressure-sensitive material, the pressure-sensitive material including dynamic, pressure-measuring indicia, wherein the pressure-measuring indicia is responsive to the application of a pressure above the predetermined threshold level to change a physical characteristic and thereby indicate the amount of pressure applied to the pressure-sensitive material.

15. The pressure-sensitive balloon catheter of claim 14, wherein the pressure-sensitive material comprises a pressure-sensitive film.

16. The pressure-sensitive balloon catheter of claim 15, wherein the pressure-sensitive film is mounted on an outer surface of the balloon.

17. The pressure-sensitive balloon catheter of claim 15, wherein the pressure-sensitive film is mounted on an inner surface of the balloon.

18. The pressure-sensitive balloon catheter of claim 15, wherein:
   the balloon comprises a first layer and a second layer; and
   the pressure-sensitive film is disposed between the first layer of the balloon and the second layer of the balloon.

19. The pressure-sensitive balloon catheter of claim 14, wherein the pressure-sensitive material comprises a pressure-sensitive coating.

20. The pressure-sensitive balloon catheter of claim 19, wherein the pressure-sensitive coating is disposed on an outer surface of the balloon.

21. The pressure-sensitive balloon catheter of claim 19, wherein the pressure-sensitive coating is disposed on an inner surface of the balloon.

22. The pressure-sensitive balloon catheter of claim 14, wherein the change in a physical characteristic is a change in color.

23. The pressure-sensitive balloon catheter of claim 22, wherein the change in color is visually perceptible.

24. A pressure-sensitive balloon catheter, comprising:
   a catheter having a distal end and an inflation lumen;
   a balloon mounted to the distal end of the catheter, the balloon being in fluid communication with the lumen, wherein the inflation lumen is operative to inflate the balloon; and
   a pressure-sensitive material mounted to the balloon, the pressure-sensitive material comprising a pressure-sensitive coating applied to the balloon, wherein the pressure-sensitive material undergoes a change in a physical characteristic when exposed to pressure.

25. The pressure-sensitive balloon catheter of claim 24, wherein the pressure-sensitive coating is disposed on an outer surface of the balloon.

26. The pressure-sensitive balloon catheter of claim 24, wherein the pressure-sensitive coating is disposed on an inner surface of the balloon.

27. A pressure-sensitive balloon catheter, comprising;
   a catheter having a distal end and an inflation lumen;
   a balloon mounted to the distal end of the catheter, the balloon comprising a first layer and a second layer and being in fluid communication with the lumen, wherein the inflation lumen is operative to inflate the balloon; and
   a pressure-sensitive material fixedly associated with the balloon, the pressure-sensitive material comprising a pressure-sensitive film disposed on one of an inner surface of the balloon or between the inner and outer layers of the balloon, wherein the pressure-sensitive material undergoes a change in a physical characteristic when exposed to pressure.

28. The pressure-sensitive balloon catheter of claim 27, wherein the change in a physical characteristic is a change in color.

29. The pressure-sensitive balloon catheter of claim 28, wherein the change in color is visually perceptible.

30. A pressure-sensitive balloon structure for use in medical dilatation procedures, comprising:
   a balloon comprising a polymeric material;
   means for inflating the balloon; and
   a pressure-sensitive material fixedly associated with the balloon, wherein the pressure-sensitive material under goes a change in a physical characteristic when exposed to pressure to indicate the amount of pressure applied to the balloon.

31. A pressure-sensitive balloon structure for use in medical dilatation procedures, comprising:
   a balloon comprising a translucent polymeric material, a plurality of microcapsules, and a color-developing material, wherein the microcapsules are adapted to rupture upon the application of pressure to indicate the amount of pressure applied to the balloon; and
   means for inflating the balloon.

* * * * *